United States Patent [19]
Ellis et al.

[11] Patent Number: 5,550,165
[45] Date of Patent: Aug. 27, 1996

[54] PHARMACEUTICAL COMPOSITIONS FOR THE TREATMENT OF HEREDITARY TYOSINEMIA TYPE I

[75] Inventors: Martin K. Ellis, Macclesfield, England; Sven T. Lindstedt, Lund, Sweden; Edward A. Lock, Wilmslow, England; Maj E. H. Markstedt, Billdal, Sweden; Linda C. Mutter, Bloomfield; Michael P. Prisbylla, Richmond, both of Calif.

[73] Assignee: Zeneca Limited, London, England

[21] Appl. No.: 359,361

[22] Filed: Dec. 19, 1994

Related U.S. Application Data

[63] Continuation of Ser. No. 903,691, Jun. 24, 1992, abandoned.

[30] Foreign Application Priority Data

Jun. 24, 1991 [GB] United Kingdom .................. 9113622
Mar. 24, 1992 [GB] United Kingdom .................. 9206412

[51] Int. Cl.⁶ ................................................. A61K 31/12
[52] U.S. Cl. ............................................................ 514/676
[58] Field of Search ............................................. 514/676

[56] References Cited

U.S. PATENT DOCUMENTS 4,774,360  9/1988  Bay ............................................ 568/306
4,780,127  10/1988  Michaely et al. ........................ 71/100

FOREIGN PATENT DOCUMENTS 0186118  7/1986  European Pat. Off. ........ C07C 79/36

OTHER PUBLICATIONS

J. Pediatr Gastroenterol Nutr. vol. 17, No. 3, 1993.
Lancet 1992; vol. 340, 813–817, Oct. 1992.
International Preliminary Report of PCT/GB92/01094, 1993.
International Search Report of PCT/GB92/01094, 1992.

Primary Examiner—Marianne M. Cintins
Assistant Examiner—William R. A. Jarvis
Attorney, Agent, or Firm—Michael D. Alexander; Ruth H. Newtson

[57] ABSTRACT

The invention concerns novel pharmaceutical compositions containing as an active ingredient a 2-benzoyl-1,3-cyclohexanedione which is an inhibitor of the enzyme 4-hydroxyphenylpyruvate dioxygenase (HPPD). The compositions are valuable in the treating those disorders and diseases in which it is desirable to intervene in the metabolic sequences catalysed by HPPD, such as in treating tyrosinemia type I.

10 Claims, 1 Drawing Sheet

PHARMACEUTICAL COMPOSITIONS FOR THE TREATMENT OF HEREDITARY TYOSINEMIA TYPE I

This is a continuation of application Ser. No. 07/903,691 filed on Jun. 24, 1992, now abandoned.

TECHNICAL FIELD

This invention concerns pharmaceutical compositions and, more particularly, it concerns compositions comprising as active agent a compound which inhibits the enzyme 4-hydroxyphenylpyruvate dioxygenase (HPPD). The compositions are of value, for example, in the treatment of disorders and diseases in which intervention in the metabolic sequences catalysed in part by HPPD is desirable, for example, in the condition known as tyrosinaemia (type I).

BACKGROUND TO THE INVENTION

Hereditary tyrosinaemia (type I) is an inborn error of metabolism. Patients suffer from multi-organ symptoms and may develop severe liver failure at a very early age, or more progressively liver disease which leads to nodular cirrhosis and the development of primary hepatic carcinoma. Damage to the kidneys and blood forming organs may also occur. Death usually occurs before the age of 20, but single patients have reached higher ages. Some patients develop symptoms characteristic of acute porphyria with episodes of acute abdominal pain and a generalised paresis. The excretion of 5-aminolevulinic acid (a precursor of porphyrins) is elevated. A porphyric episode may be the cause of death. There is no impairment of intelligence or central nervous system function. The incidence in Sweden is about 1 in 100,000 births. However, in certain regions of Canada the incidence is higher, for example, in the Lac-St Jean area of Quebec, it is about 1 in 1800 births.

The disease was named following the initial finding of high tyrosine concentrations in blood and the excretion of 'phenolic acids' in urine. Originally it was supposed that the primary enzyme defect was a deficiency of HPPD, which enzyme is responsible for catalysing the conversion of 4-hydroxyphenylpyruvate (the primary product of the action of tyrosine aminotransferase) to homogentisate. However, it was noted that those patients with a considerable residual activity of this enzyme had a more severe form of the disease.

Patients with hereditary tyrosinaemia (type I) excrete succinylacetoacetate and succinylacetone as well as 5-aminolevulinic acid. The plasma concentration of α-fetoprotein is often high and a dramatic increase in this protein may indicate the development of liver cancer. Succinylacetoacetate may be formed from fumaryl-acetoacetate, which is normally hydrolysed by the enzyme fumarylacetoacetase and also from maleylacetoacetate (the product of the action of homogentisate 1,2-dioxygenase on homogentisate). Based on the excretion of succinylacetoacetate and succinylacetone by patients with hereditary tyrosinaemia (type I), Lindstedt and co-workers (*Proc. Natl. Acad. Sci.,* 1977, 74, 4641–4645) have concluded that the primary defect in the disease is a deficiency in the enzyme fumarylacetoacetase.

The biochemical inter-relationship of the products of tyrosine metabolism is shown for information in FIG. 1. Succinylacetone is a powerful inhibitor of porphobilinogen synthase which catalyses the formation of porphobilinogen from 5-aminolevulinic acid in the haem biosynthetic pathway. This provides an explanation for the elevated excretion of 5-aminolevulinic acid and the porphyric symptoms.

The principal treatment of hereditary tyrosinaemia (type I) is based on restricting tyrosine dietary intake. This is not normally effective in preventing the fatal outcome of the disease. Liver transplantation may be performed in some patients producing some amelioration of the disease. However, since tyrosine degradation occurs in both the liver and the kidneys, liver transplantation may not prevent the development of severe kidney damage frequently associated with tyrosinaemia (type I). Accordingly, there is a continuing need for an effective means of treating diseases and related conditions such as tyrosinaemia (type I).

It has now been discovered (and this is the basis for the invention) that the compound 2-(2-nitro-4-trifluoromethylbenzoyl)-1,3-cyclohexanedione is an inhibitor of the catalytic activity of the enzyme HPPD and may be useful in the treatment of diseases where the products of the action of HPPD are involved, for example in treating tyrosinaemia (type I).

DISCLOSURE OF THE INVENTION

According to the invention there is provided a pharmaceutical composition comprising as an active ingredient the compound: 2-(2-nitro-4-trifluoromethylbenzoyl)-1,3-cyclohexanedione (hereinafter referred to as "the Compound"), or a pharmaceutically acceptable salt thereof, together with a pharmaceutically acceptable diluent or carrier.

It will be appreciated that the Compound may exist in one or more tautomeric forms, one of which is shown in formula I:

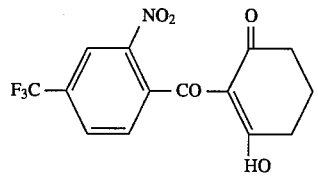

and which forms are readily interconvertible by keto-enol tautomerism. It is to be understood that the invention includes the use of the Compound in any of such tautomeric forms or as a mixture thereof.

The Compound is acidic and readily forms salts with a wide variety of bases. Particularly suitable salts of the Compound suitable for use as active ingredients in pharmaceutical compositions according to the invention include, for example, pharmaceutically acceptable base-addition salts, for example, alkali metal (such as potassium or sodium), alkaline earth metal (such as calcium or magnesium) and ammonium salts, and salts with organic bases giving physiologically acceptable cations (such as salts with methylamine, dimethylamine, trimethylamine, piperidine and morpholine).

The Compound may be obtained by conventional procedures of organic chemistry already known for the production of structurally analogous materials. Thus, for example, the Compound may be conveniently obtained by reaction of 2-nitro-4-trifluoromethylbenzoyl chloride with cyclohexane-1,3-dione in the presence of acetone cyanhydrin and a suitable base such as triethylamine, as is illustrated in Example 1 hereinafter. The starting 2-nitro-4-trifluoromethylbenzoyl chloride may itself be obtained from the corresponding benzoic acid, for example by reaction with thionyl chloride or oxalyl chloride as is described in *Reagents for Organic Synthesis,* (J Wiley and Sons, 1967; editors: Fieser L. F. and Fieser M.; Vol 1, pp. 767–769) and is generally used without special purification. Similarly, 2-nitro-4-trifluoromethylbenzoic acid may be obtained, for example, as described by Haupstein et al. in *J. Amer. Chem. Soc.*, 1954, 76, 1051, or by one of the general methods described in *The Chemistry of Carboxylic Acids and Esters* (J Wiley and Sons, 1969; editor: S. Patai) and *Survey of Organic Synthesis* (J Wiley and Sons, 1970; C. A. Buehler and D. F. Pearson).

The compositions of the invention may be in various conventional forms well know in the pharmaceutical art and which are especially adapted for pharmaceutical purposes that is for administration to man and other warm-blooded animals. Thus, they may be in a palatable form suitable for oral use (for example as tablets, lozenges, hard or soft capsules, aqueous or oily suspensions, emulsions, dispersible powders or granules, syrups or elixirs), or for parenteral administration (for example as a sterile aqueous or oily solution for intravenous, subcutaneous, intramuscular or intravascular dosing), or for rectal dosing as a suppository.

The compositions of the invention may be obtained by conventional procedures using conventional pharmaceutical excipients, well known in the art. Thus, compositions intended for oral use will normally contain, for example, at least one or more colouring, sweetening, flavouring and/or preservative agents and may be in the form of hard gelatin capsules in which the active ingredient is mixed with an inert solid diluent, for example, calcium carbonate, calcium phosphate or kaolin, Compositions for oral use may also be in the form of soft gelatin capsules in which the active ingredient is mixed with water or an oil such as arachis oil, liquid paraffin or olive oil.

Suitable pharmaceutically acceptable excipients for use in tablet formulations include, for example, inert diluents such as lactose, sodium carbonate, calcium phosphate or calcium carbonate, granulating and disintegrating agents such as corn starch or alginic acid; binding agents such as gelatin or starch; lubricating agents such as magnesium stearate, stearic acid or talc; preservative agents such as ethyl or propyl p-hydroxybenzoate, and anti-oxidants, such as ascorbic acid. Tablet formulations may be uncoated or coated either to modify their disintegration and the subsequent absorption of the active ingredient within the gastrointestinal tract, or to improve their stability and/or appearance, in either case, using conventional coating agents and procedures well known in the art.

Aqueous suspensions will generally contain the active ingredient in finely powdered form together with one or more pharmaceutically acceptable suspending agents, such as sodium carboxymethylcellulose, methylcellulose, hydroxypropylmethylcellulose, sodium alginate, polyvinylpyrrolidone, gum tragacanth and gum acacia; dispersing or wetting agents such as lecithin or condensation products of an alkylene oxide with fatty acids (for example polyoxyethylene stearate), or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan mono-oleate. Aqueous suspensions will also typically contain one or more preservatives (such as ethyl or propyl p-hydroxybenzoate, anti-oxidants (such as ascorbic acid), colouring agents, normally together with a flavouring and/or sweetening agent (such as sucrose, saccharin or aspartame).

Oily suspensions may be formulated by suspending the active ingredient in a vegetable oil (such as arachis oil, olive oil, sesame oil or coconut oil) or in a mineral oil (such as liquid paraffin). The oily suspensions may also contain a thickening agent such as beeswax, hard paraffin or cetyl alcohol. Sweetening agents such as those set out above, and flavouring agents may be added to provide a palatable oral preparation. These compositions may be preserved by the addition of an anti-oxidant such as ascorbic acid.

Dispersible powders and granules suitable for preparation of an aqueous suspension by the addition of water generally contain the active ingredient together with a dispersing or wetting agent, suspending agent and one or more preservatives. Suitable dispersing or wetting agents and suspending agents are exemplified by those already mentioned above. Additional pharmaceutically acceptable excipients such as sweetening, flavouring and colouring agents, will generally also be present.

The pharmaceutical compositions of the invention may also be in the form of oil-in-water emulsions. The oily phase may be a vegetable oil, such as olive oil or arachis oil, or a mineral oil, such as for example liquid paraffin or a mixture of any of these. Suitable emulsifying agents may be, for example, naturally-occurring gums such as gum acacia or gum tragacanth, naturally-occurring phosphatides such as soya bean, lecithin, or esters or partial esters derived from fatty acids and hexitol anhydrides (for example sorbitan monooleate) and condensation products of the said partial esters with ethylene oxide such as polyoxyethylene sorbitan monooleate. The emulsions may also contain sweetening, flavouring and preservative agents.

Syrups and elixirs may be formulated with sweetening agents such as glycerol, propylene glycol, sorbitol, aspartame or sucrose, and may also contain a demulcent, preservative, flavouring and/or colouring agent.

The pharmaceutical compositions may also be in the form of a sterile injectable aqueous or oily suspension, which may be formulated according to known procedures using one or more of the appropriate dispersing or wetting agents and suspending agents, which have been mentioned above. A sterile injectable preparation may also be a sterile injectable solution or suspension in a non-toxic parenterally-acceptable diluent or solvent, for example a solution in 1,3-butanediol.

Suppository formulations may be prepared by mixing the active ingredient with a suitable non-irritating excipient which is solid at ordinary temperatures but liquid at the rectal temperature and will therefore melt in the rectum to release the drug. Suitable excipients include, for example, cocoa butter and polyethylene glycols.

The amount of active ingredient that is combined with one or more excipients to produce a single dosage form will necessarily vary depending upon the host treated and the particular route of administration. For example, a formulation intended for oral administration to humans will generally contain for example from 0.5 mg to 200 mg of active agent combined with an appropriate and convenient amount of excipients which will typically vary from about 10 to about 98 percent by weight of the total composition. Dosage unit forms will generally contain about 1 mg to about 400 mg of an active ingredient. However, it will be readily understood that it may be necessary to vary the dose of the active ingredient administered in accordance with well known medical practice in order to take account of the nature and severity of the condition or disease under treatment, any concurrent therapy, and of the age, weight and sex of the patient receiving treatment.

According to another aspect of the invention, there is provided a method of treatment of a disorder or disease affecting a warm blooded animal such as man in which intervention in the metabolic sequences catalysed in part by the enzyme HPPD is desirable, by administration of an effective amount of the Compound (as defined hereinbefore), or of a pharmaceutically acceptable salt thereof. For example, the treatment of the disorder known as tyrosinaemia (type I) by administration of the Compounds or of a pharmaceutically acceptable salt thereof is provided according to a particular aspect of the invention.

As a further aspect of the invention, there is provided the use of the Compound (as defined hereinbefore), or of a pharmaceutically acceptable salt thereof, in the manufacture of a human or veterinary medicament for the treatment of a disorder or disease affecting a warm blooded animal such as man in which intervention in the metabolic sequences catalysed in part by the enzyme HPPD is desirable. One such disorder or disease is that known as tyrosinaemia (type I).

The activity of the compounds of formula I in inhibiting the catalytic actions of the enzyme HPPD may be assessed in the laboratory using one or more standard procedures.

One such procedure involves monitoring the oxygen consumption of the rat liver enzyme in the presence of its substrate, 4-hydroxyphenylpyruvate. A typical assay according to this procedure uses an oxygen electrode with 0.2M sodium phosphate buffer at pH 7.2 (3.8 mL) in the reaction vessel at 37° C. Ascorbate (about 7 µM final concentration) and rat liver cytosol (105,000×g supernatant-about 0.2 mL, equivalent to 5 mg of protein) are then added. After equilibration to 37° C. for 3–5 minutes, the enzymatic reaction is started by the addition of the substrate, 4-hydroxyphenylpyruvate (about 200 µM final concentration). A test substance may be evaluated in this assay either by incubation with the enzyme for about 5 minutes prior to starting the reaction with substrate or by injecting the test active ingredient into the reaction vessel together with the substrate.

Alternatively, an assay based on that described by Lindstedt and co-workers (*Methods in Enzymology*, 1987, 142, 139–142 and 143–148) and involves monitoring the effects of a test substance on the release of $^{14}CO_2$ from 4-hydroxyphenyl(1–$^{14}C$)pyruvate using rat or human liver cytosol as the enzyme source.

Typically, the Compound, or a pharmaceutically acceptable salt thereof, has been found to show significant inhibition of the enzyme in one of the above assays (i.e. >30% inhibition of oxygen uptake and/or >30% reduction in release of $^{14}CO_2$) at concentrations of 100 nM or less. The Compound is not in general particularly toxic to warm blooded animals. Thus, it shows no significant toxic or other adverse effects when administered to rhesus monkeys over 90 days at a daily oral dose of 10 mg/kg.

In therapeutic use, it is envisaged that a composition according to the invention would be administered so that a dose of the Compound (or of an equivalent amount of a pharmaceutically acceptable salt thereof) is received which is generally in the range 0.01 to 10 mg/kg daily (and preferably in the general range 0.05 to 5 mg/kg daily) given if necessary in divided doses. Intermittent dosing of the Compound (or of a pharmaceutically acceptable salt thereof) may also be desirable. In addition to assessment of the overall condition of the patient, the effects of administration of the the Compound or a salt thereof may be monitored by standard clinical chemical and blood assays to assess the effects on levels of tyrosine metabolites and porphobilinogen synthase activity, for example, as mentioned in the accompanying Examples.

The utility of the Compound or a salt thereof in the treatment of a disorder or disease affecting a warm blooded animal such as man in which intervention in the metabolic sequences catalysed at least in part by the enzyme HPPD is desirable, may be demonstrated in conventional therapeutic intervention trials, in which improvement in clinical and biochemical parameters. Thus, utility in the treatment of tyrosinaemia (type I) may be assessed, for example, by monitoring over a period of several months one or more of the biochemical markers of the disease. For example, these will typically include α-fetoprotein and other standard indicators of liver dysfunction. In addition, improvement in porphobilinogen synthase activity and/or reduction in urinary 5-aminolevulinic acid levels are particularly good markers of early clinical efficacy. An illustrative clinical protocol is provided in the accompanying Examples.

Figure 1:
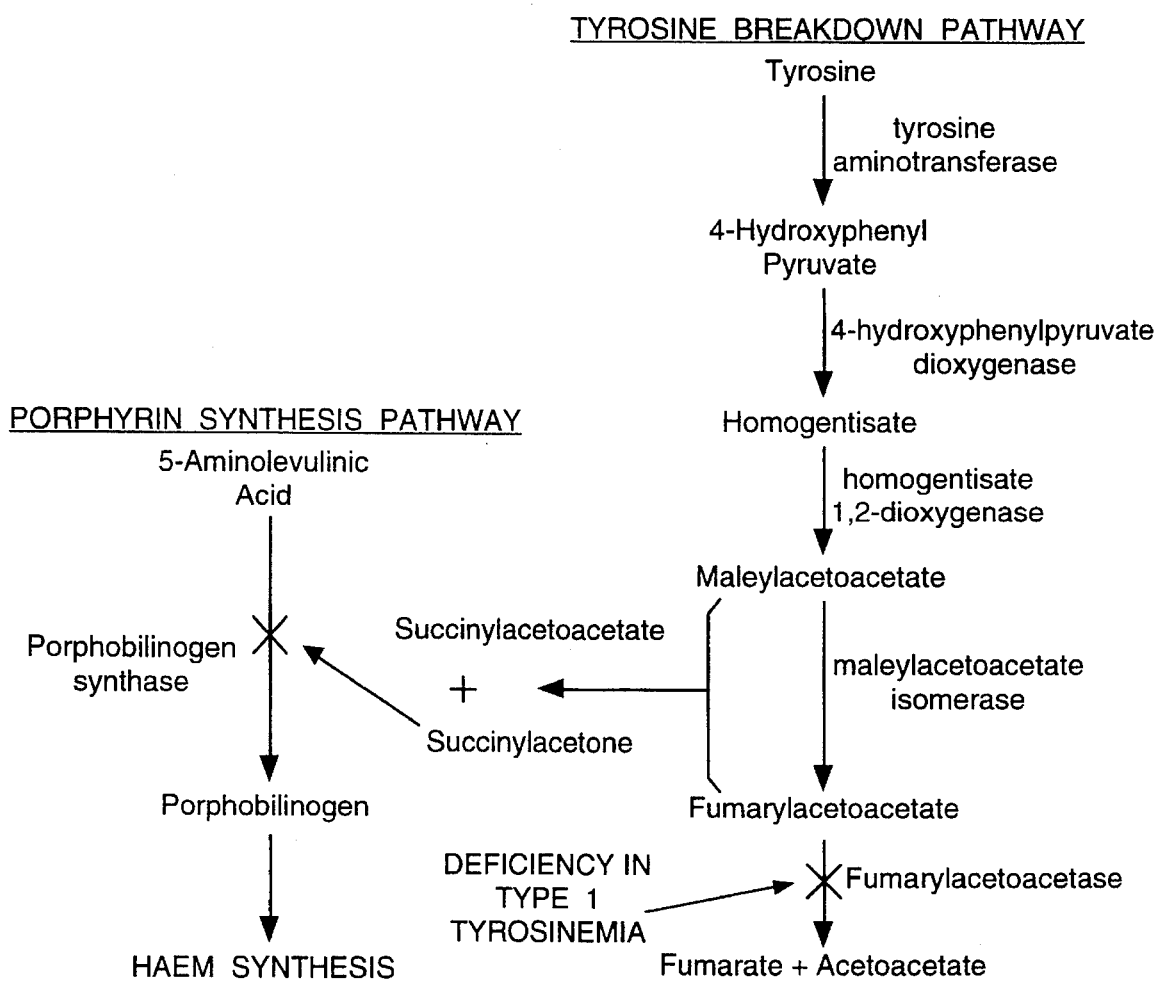
FIG. 1 shows the biochemical interrelationship of the products of tyrosine metabolism.

The invention will now be illustrated by the following non-limiting Examples:

EXAMPLE 1

[This Example describes a procedure for the preparation of the Compound]

Triethylamine (3.4 mL, 25 mM) is added dropwise to a stirred solution of 2-nitro-4-trifluromethylbenzoyl chloride (19 mM; itself obtained by reaction of 2-nitro-4-trifluoromethylbenzoic acid with an excess of oxalyl chloride) and cyclohexane-1,3-dione (19 mM) in dichloromethane (100 mL). The mixture is stirred for one hour at ambient temperature and then further triethylamine (57 mM) and acetone cyanohydrin (0.4 mL) is added. Stirring is continued for a further 2.5 hours and then the mixture is washed thoroughly with 2M hydrochloric acid to remove triethylamine. The organic phase is then extracted thoroughly with potassium carbonate (5% w/v). The combined basic extracts are then acidified with 2M hydrochloric acid and extracted with ether. The ether extracts are washed with saturated sodium chloride solution, dried (magnesium sulphate) and the volatile material removed by rotary evaporation in vacuo. There may thus be obtained 2-(2-nitro-4-trifluoromethylbenzoyl)-1,3-cyclohexanedione as a solid, m.p. 88°–84° C. (recrystallised from ethyl acetate) having a satisfactory microanalysis and infra-red and proton magnetic resonance spectra.

EXAMPLE 2

The following illustrate representative pharmaceutical dosage forms containing the Compound, or a pharmaceutically acceptable salt thereof, (referred to as "Active Ingredient") for therapeutic or prophylactic use in humans:

| (a) Tablet I | mg/tablet |
|---|---|
| Active Ingredient | 50 |
| Lactose Ph.Eur | 223.75 |
| Croscarmellose sodium | 6.0 |
| Maize starch | 15.0 |
| Polyvinylpyrrolidone (5% w/v paste) | 2.25 |
| Magnesium stearate | 3.0 |

| (b) Tablet II | mg/tablet |
|---|---|
| Active Ingredient | 1.0 |
| Lactose Ph.Eur | 93.25 |
| Croscarmellose sodium | 4.0 |
| Maize starch paste (5% w/v paste) | 0.75 |
| Magnesium stearate | 1.0 |

| (c) Capsule | mg/capsule |
|---|---|
| Active Ingredient | 10 |
| Lactose Ph.Eur | 488.5 |
| Magnesium stearate | 1.5 |

The above formulations may be obtained by conventional procedures well known in the pharmaceutical art. Tablets I and II may, if required, be conveniently enteric coated by conventional means, for example, with a coating of cellulose acetate phthalate.

EXAMPLE 3

[This Example describes a typical protocol for clinical evaluation of a composition of the Compound in tyrosinaemia (type I).]

Patients with an advanced form of the disease will be given the test composition (generally about 0.2–2.0 mg of active ingredient per kg body weight) orally. A blood sample will be taken daily during the first week and then less frequently at the discretion of the physician. Urine specimens will normally be collected daily. The indicators outlined below will be used to monitor the response to the test composition. The treatment will be maintained for up to 12 months if a clinically and biochemically satisfactory response is observed. If not, the dose of active ingredient administered will be increased stepwise to a maximum of about 2 mg/kg per day. Should any adverse indication occur, based on the biochemical monitoring or clinical assessment dosing will be stopped immediately.

The patients will be placed on a tyrosine-restricted diet with the aim of keeping plasma tyrosine concentrations below 500 μmol/L. A large increase in the tyrosine concentration in plasma is not expected to occur, but levels will be monitored throughout the dosing. Changes in the excretion of the biochemical markers mentioned below, such as succinylacetoacetate, succinylacetone and 5-aminolevulinic acid will be monitored, as will the effect on porphobilinogen synthase and α-fetoprotein concentration.

Biochemical markers:

Tyrosine and Methionine—these amino acids will be determined in plasma by a standard technique using an amino-acid analyser.

Succinylacetoacetate and Succinylacetone—these compounds will be determined in urine by gas chromatography—mass spectrometry. Succinylacetone in plasma will be determined by measuring the inhibition of porphobilinogen synthase using a conventional assay.

5-Aminolevulinic acid—this will be determined in urine by a conventional colorimetric assay.

p-Hydroxyphenylpyruvate and p-hydroxyphenyllactate—these compounds will be determined in urine by convention gas chromatographic methods.

α-Fetoprotein—this will be determined in plasma by a conventional radioimmunoassay technique.

Porphobilinogen synthase—this will be determined in erythrocytes using a conventional colorimetric assay.

Clinical chemistry, haematology and coagulation parameters—these will be determined by standard methods.

EXAMPLE 4

[This Example describes the therapeutic evaluation of a composition according to the invention.]

Patient 1:

A female patient (age 2 months) was admitted to hospital after problems with slight nose bleedings and the parents noting swelling of the abdomen. Metabolic screening in hospital diagnosed tyrosinaemia (type I) based on the abnormal excretion of succinylacetone, succinylacetoacetate and 5-aminolevulinic acid in urine and a low activity of porphobilinogen synthase in erythrocytes. Treatment was started using essentially the protocol described in Example 3 using a capsule formulation of the Compound (active ingredient 0.08 mg/b.w.). This was increased to 0.16 mg/kg b.w. after four days, and then to about 0.4 mg/kg by the end of the first 2 months, the dose being divided into two portions for morning and afternoon administration. The dose was then increased to about 0.6 mg/kg after a further 5 months. The following observations were made:

(a) There was an immediate increase in porphobilinogen synthase activity in erythrocytes with a concomitant decrease in the excretion of 5-aminolevulinic acid.

(b) There was an immediate decrease in the excretion of succinylacetone and succinylacetoacetate (from 50 mmol/mol of creatinine to a level of <1 mmol/mol of creatinine) and a similar immediate decrease in plasma succinylacetone levels (to the limit of detection, after about 30 days).

(c) Methionine concentration in plasma which was very high initially and decreased somewhat on diet dropped to normal levels very rapidly after start of treatment.

(d) The concentration of amino acids in urine was very high before treatment and decreased (5–10 times) after treatment.

(e) Although liver function was initially compromised by a concomittant cytomegalovirus infection, markers of liver dysfunction progressively improved during dosing e.g. serum α-fetoprotein concentration decreased from 7,200 μg/L to 96 μg/L.

(f) The overall clinical condition of the patient improved markedly during the treatment period enabling the patient to be discharged from hospital. Dosing is continuing.

Patient 2:

A male patient (age 5 years) was dosed 0.2 mg/kg b.w. of a capsule formulation of the Compound. During the initial 3 month dosing period, porphobilinogen synthase activity increased to normal levels. Similarly, during the treatment period urinary levels of succinylacetone and 5-aminolevulinic acid and serum levels of succinylacetone and α-fetoprotein decreased, the latter significantly (from ca. 900 to 40 μg/L) and the clinical position of the patient improved. Dosing is continuing.

Patient 3:

A male patient (age 6 years) was dosed 0.2 mg/kg b.w. of a capsule formulation of the Compound. After 5 months, this dose was increased to 0.6 mg/kg b.w. given in two divided doses. During this period urinary and plasma levels of succinylacetone and urinary levels of 5-aminolevulinic acid were all substantially lowered. Similarly, serum levels of α-fetoprotein fell substantially (from ca. 900 to 11 μg/L) and the clinical position of the patient improved.

Patient 4:

A male patient (age 3 years) was dosed 0.2 mg/kg b.w. of a capsule formulation of the Compound. After 5 months, this dose was increased to 0.6 mg/kg b.w. given in two or three divided doses. During this period urinary and plasma levels of succinylacetone and urinary levels of 5-aminolevulinic acid were all substantially lowered. Similarly, serum levels of α-fetoprotein fell substantially (from ca. 2000 to 48 μg/L) and the clinical position of the patient improved.

What is claimed is:

1. A pharmaceutical composition comprising as an active ingredient an effective 4-hydroxyphenypyruvate dioxygenase inhibiting amount of the compound 2-(2-nitro-4 -trifluoromethylbenzoyl)-1,3-cyclohexanedione, or a pharmaceutically acceptable salt thereof, together with a pharmaceutically acceptable diluent or carrier.

2. A composition as claimed in claim 1 wherein the active ingredient is selected from an alkali metal salt, alkaline earth metal salt, ammonium salt, and a salt with an organic base giving a physiologically acceptable cation, of the compound 2-(2-nitro-4-trifluoromethylbenzoyl)-1,3-cyclohexanedione.

3. A composition as claimed in claim 1 or 2 which is in a form suitable for oral, parenteral or rectal administration.

4. A composition as claimed in claim 1 or 2 which is in a palatable form suitable for oral administration selected from tablets, lozenges, hard capsules, soft capsules, aqueous suspensions, oily suspensions, emulsions, dispersible powders, dispersible granules, syrups and elixirs.

5. A composition as claimed in claim 1 or 2 which is in a form suitable for parenteral administration selected from sterile aqueous and oily solutions.

6. A method of treating multi-organ symptoms in human patients caused by hereditary tyrosinaemia in which intervention in the metabolic sequences catalysed in part by the enzyme 4-hydroxyphenylpyruvate dioxygenase is desirable which comprises the administration of an effective amount of 2-(2-nitro-4-trifluoromethylbenzoyl)-1,3-cyclohexandione, or a pharmaceutically acceptable salt thereof.

7. A method for the treatment of the disease condition known as hereditary tyrosinaemia in a warm blooded animal which comprises the administration of an effective amount of 2-(2-nitro-4-trifluoromethylbenzoyl)-1,3-cyclohexanedione, or of a pharmaceutically acceptable salt thereof.

8. A pharmaceutical composition according to claim 1 wherein the pharmaceutically acceptable carrier is selected from Lactose Ph.Eur; croscarmellose sodium; maize starch, polyvinylpyrrolidone or magnesium stearate.

9. A method of inhibiting the catalytic activity of the enzyme 4-hydroxyphenylpyruvate dioxygenase comprising the administration to a human patient in need of treatment thereof suffering from hereditary tyrosinaemia and associated symptoms a therapeutically effective amount of the compound 2-(2-nitro-4-trifluoromethylbenzoyl)-1,3-cyclohexandione or a pharmaceutically acceptable salt thereof.

10. A method of treating hereditary tyrosinaemia in human patients wherein the products of the catalytic action of the enzyme HPPD are involved or implicated comprising the administration of a pharmaceutically effective amount of the compound 2-(2-nitro-4-trifluoro-methylbenzoyl)-1,3-cyclohexanedione or a pharmaceutically acceptable salt thereof.

* * * * *